Figure 1:
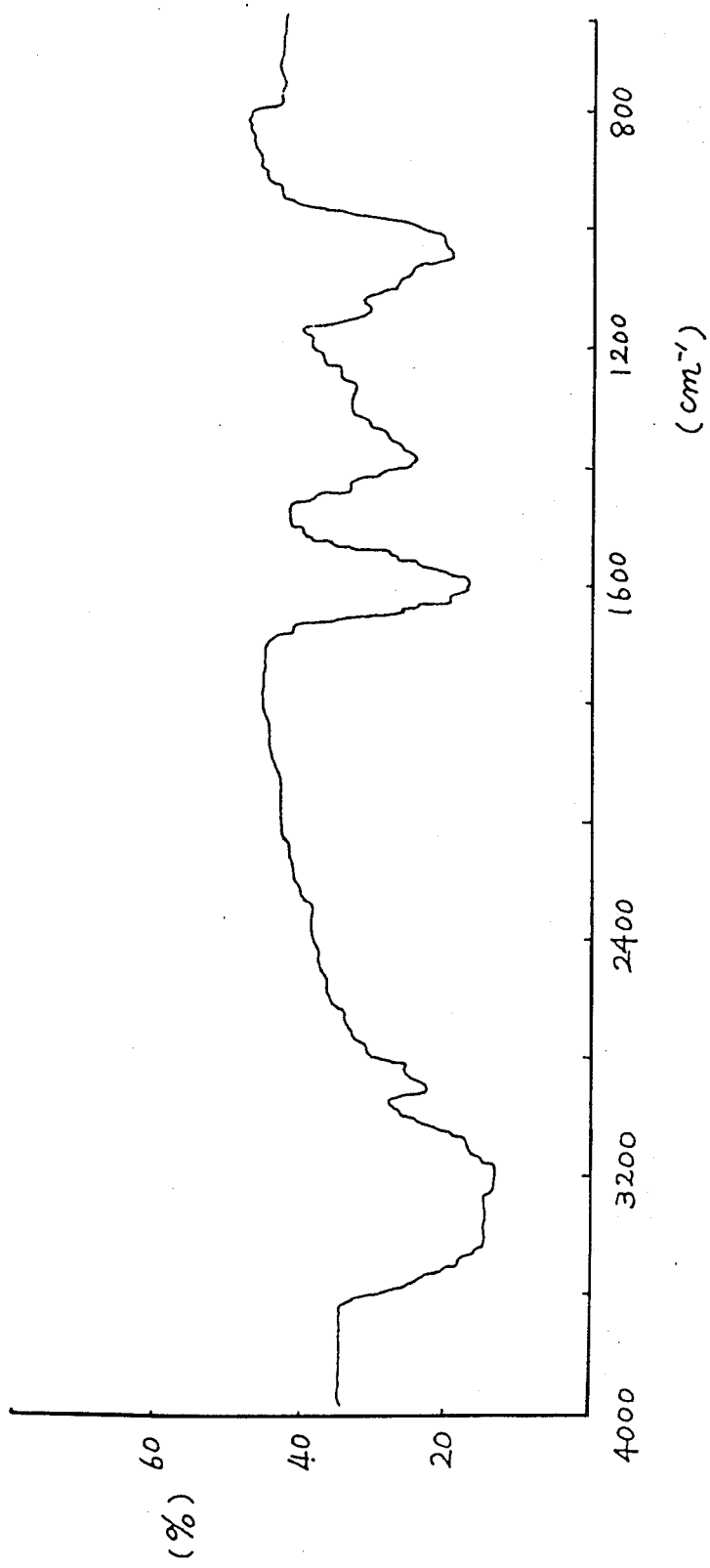

United States Patent [19]

Kidani et al.

[11] Patent Number: 4,551,524

[45] Date of Patent: Nov. 5, 1985

[54] PLATINUM COMPLEXES OF GLUCURONIC ACID

[75] Inventors: Yoshinori Kidani; Masahide Noji, both of Nagoya, Japan

[73] Assignee: Yoshinori Kidani, Nagoya, Japan

[21] Appl. No.: 507,243

[22] Filed: Jun. 23, 1983

[30] Foreign Application Priority Data

Jun. 24, 1982 [JP] Japan ................................ 57-108925

[51] Int. Cl.⁴ ...................... C07H 11/00; C07H 23/00
[52] U.S. Cl. ..................................... 536/121; 556/136
[58] Field of Search ..................... 536/121; 260/429 R

[56] References Cited

U.S. PATENT DOCUMENTS 4,200,583 4/1980 Kidani et al. ................... 260/429 R
4,203,912 5/1980 Hydes et al. .................... 260/429 R

OTHER PUBLICATIONS

Noji et al., "Chem. Abst." vol. 98, 1983 pp. 118447(c).
Noji et al., "Chemistry Letters", 1982, pp. 1757–1760.

Primary Examiner—Johnnie R. Brown
Attorney, Agent, or Firm—Wolder, Gross & Yavner

[57] ABSTRACT

The invention relates to compounds that are complexes of diaminocyclohexane platinum glucuronic acid halide and the use of these compounds as anti-tumor agents for lower animals.

5 Claims, 7 Drawing Figures (min)

PLATINUM COMPLEXES OF GLUCURONIC ACID

This invention relates to new platinum complexes having anti-tumour activity and low toxicity.

This invention provides a new platinum complex represented by the general formula (I):

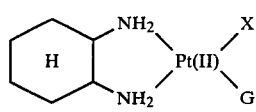

wherein X is a halogen atom and G is a glucuronic acid residue (hereinafter referred to as D-gluc) of the formula:

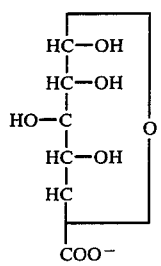

the configuration of diaminocyclohexane being selected from cis-, trans-l- and trans-d-forms.

It is known that certain platinum complexes are active against tumour cells [for example, Nature, 222, 385 (1969); Platinum Rev., 15, No. 2, 42–51 (1971); ibid., 17, No. 1, 2–13 (1973) and U.S. Pat. Nos. 4,115,418; 4,196,846 and 4,200,583]. In particular, cis dichlorodiammineplatinum (II) has been found to possess anti-tumour activity, but as a result of its toxic side effect, it has a rather low therapeutic index.

This invention is based upon the discovery that the platinum complexes of the formula (I) exhibit anti-tumour activity and are potentially of interest as medicaments.

By way of examples, the compounds of the formula (I) include Pt(II)Cl(D-gluc)(dach), Pt(II)Br(D-gluc)(dach), Pt(II)I(D-gluc)(dach) and Pt(II)F(D-gluc)(dach) where X in the formula (I) represents Cl, Br, I or F. In this specification, diaminocyclohexane is referred to as "dach" and its configuration is selected from cis-, trans-l- and trans-d.

In comparison with the known platinum complexes having anti-tumour activity, the compounds of this invention, in particular Pt(II)Cl(D-gluc)(dach) exhibit moderate water-solubility and good therapeutic effects.

The compounds of the formula (I) may be prepared by the reaction of Pt(II)(D-gluc)$_2$(dach) with KX (wherein X is as hereinbefore defined). The reaction may conveniently be effected in water, for example, at a temperature of from 0° to 15° C. for 10–20 hours. After completion of the reaction, the desired product may be recovered from the reaction solution, for example, by column chromatography using Amberlite R-120, Amberlite IRA-400 (commercial products of Rohm and Haas Co., U.S.A.), Sephadex G-10 (commercial product of Pharmacia Fine Chemicals AB., Sweden) and the like.

Pt(II)(d-gluc)$_2$(dach) used as starting material for the preparation of the compounds of the formula (I) may be obtained in conventional manner [for example, U.S. Pat. No. 4,200,583].

The following non-limiting examples illustrate the invention.

EXAMPLE 1

Pt(II)(D-gluc)$_2$(trans-l-dach) [150 mg; $2.156 \times 10^{-4}$ mo] was dissolved in water (5 ml), to which KCl (16.1 mg, dissolved in 1 ml of water) was added to effect the reaction at 5°–7° C. for about 16 hours. The reaction solution was filtered and the filtrate was passed through a column (1×15 cm) packed with Amberlite R-120 (0.5 g) and another column (1×15 cm) packed with Amberlite IRA-400 (0.5 g) to remove KCl, followed by column chromatography using a column (2.6×40 xm) packed with Sephadex G-10 (40 g) eluted with water. The resultant effluent was divided into 100 fractions (each 3.3 ml). The ultraviolet absorption at 290 nm was measured and Fraction Nos. 30–39 corresponding to the peak subsequent to the absorption indicating the starting material were collected and combined. The combined fractions were concentrated and freeze-dried to obtain Pt(II)Cl(D-gluc)(trans-l-dach) having the following pysical properties with an yield of about 20%:

| Elemental analysis: | H | C | N |
|---|---|---|---|
| Calculate | 4.54 | 25.92 | 5.04 |
| Found | 4.50 | 26.88 | 4.76 |

Figure 2:
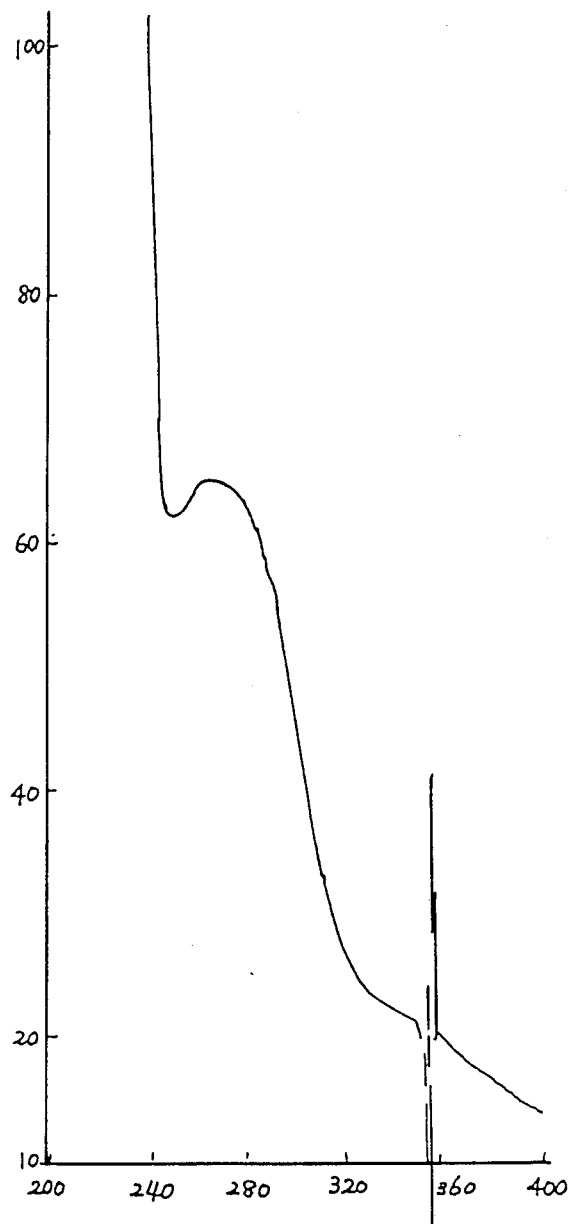
Figure 3:
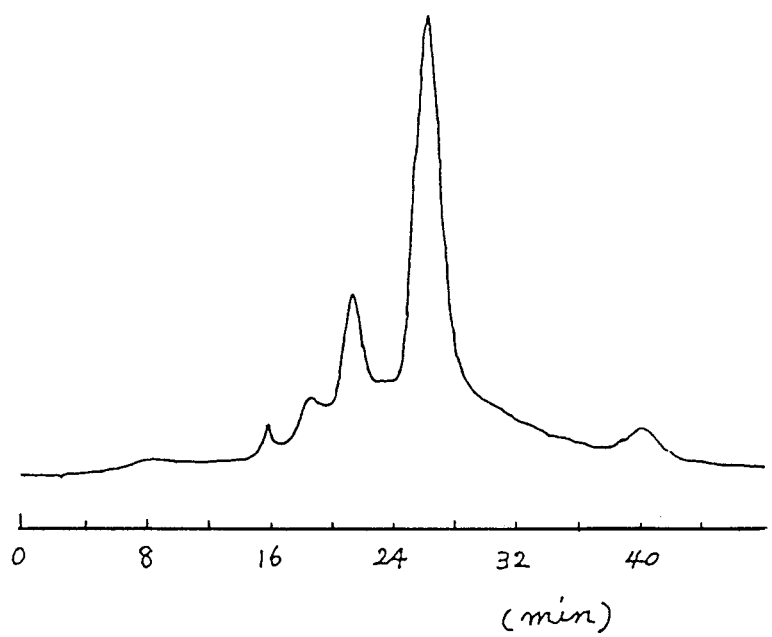

The ultraviolet and infrared absorption spectra of the product are respectively shown in FIGS. 1 and 2. A HPLC chart shown in FIG. 3 was obtained by treating the product under the following conditions:

Eluting solution: 0.1M Na$_2$SO$_4$ (pH=6.02)

Flow rate: 1.0 ml/min.

Chart speed: 2.5 mm/min.

The desired product was found by the maximum peak observed after the stay of 26.5–26.4 minutes.

The thus-obtained product exhibited the following anti-tumour activity.

CDF mice (each group consisting of 6 mice) were used as test animals. On each occasion, 10$^5$ cells of L 1210 were administered into the abdominal acvity of the animal. On the same day and 5th and 9th days after this, samples of the test compound were administered to the animals to investigate the extended survival days i.e. T/C % shown in the following table:

| Dose (mg/kg)/day | T/C % |
|---|---|
| 50 | 86 |
| 25 | 285 (4/6) |
| 12.5 | 301 (3/6) |
| 6.25 | 249 (2/6) |
| 3.12 | 150 |

EXAMPLE 2

Figure 4:
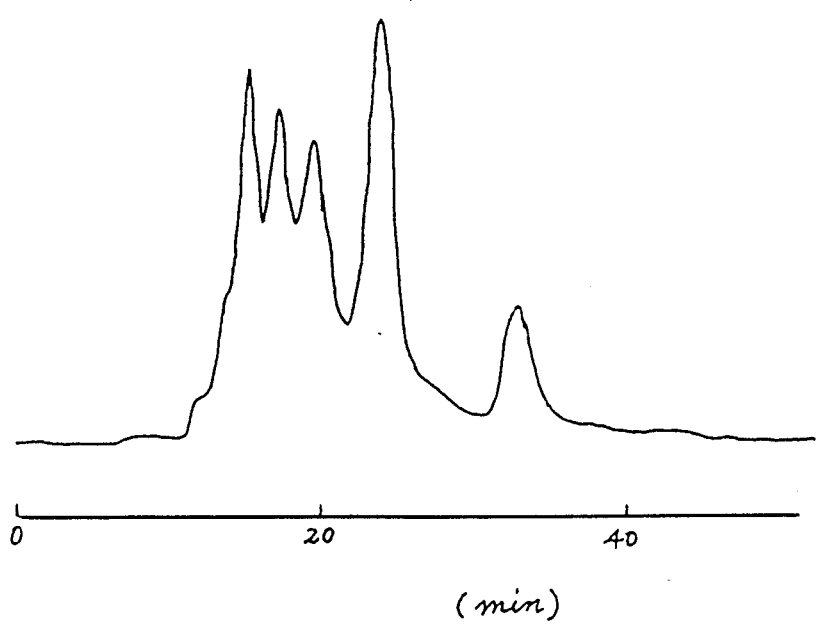
Figure 5:
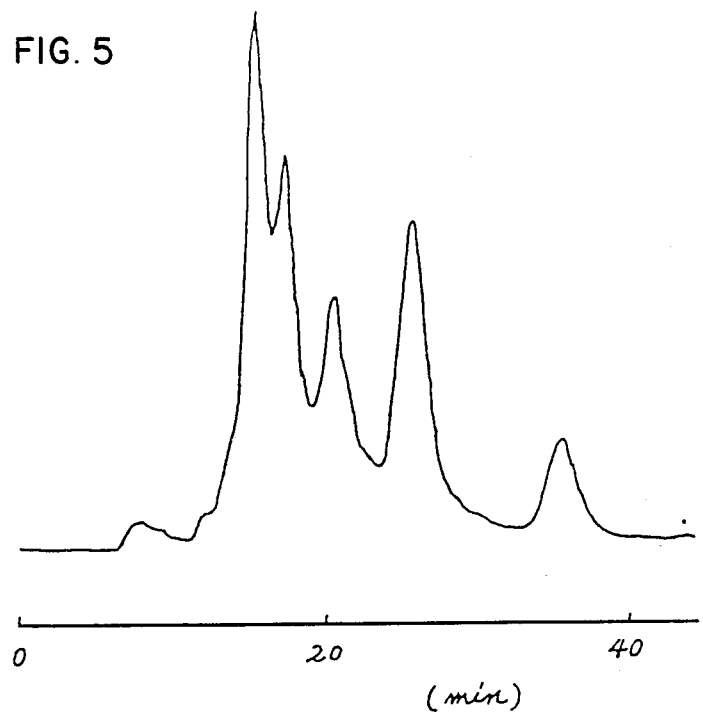

Analogous treatments to those described in Example 1 were repeated by using respectively Pt(II)(D-gluc)$_2$(cis-dach) and Pt(II)(D-gluc)$_2$(trans-d-dach) as starting compounds to obtain the HPLC charts shown respectively in FIGS. 4 and 5 by filtering the reaction solutions to obtain the filtrates which were chromatographed by HPLC. The maximum peak shown in FIG.

4 and the second peak shown in FIG. 5 (from the right hand side) show respectively Pt(II)(Cl(D-gluc)(cis-dach) and Pt(II)Cl(D-gluc)(trans-d-dach).

EXAMPLE 3

Figure 6:
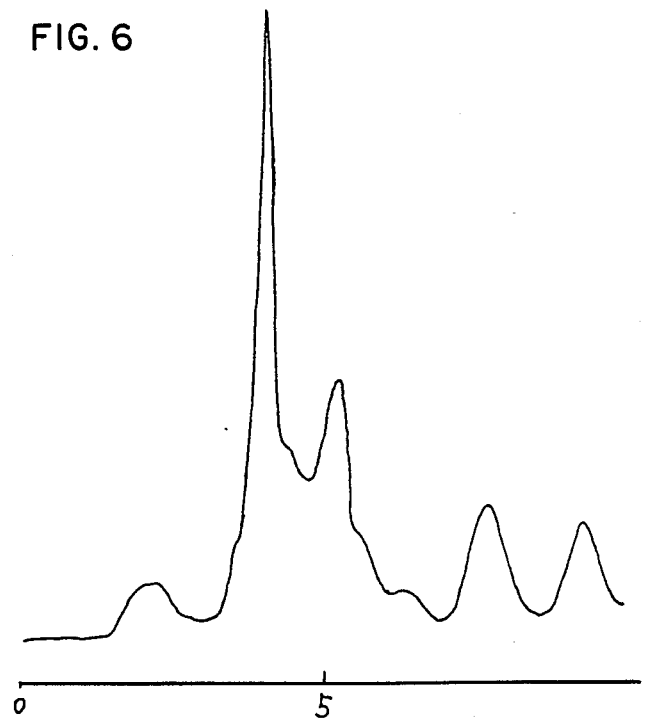
Figure 7:
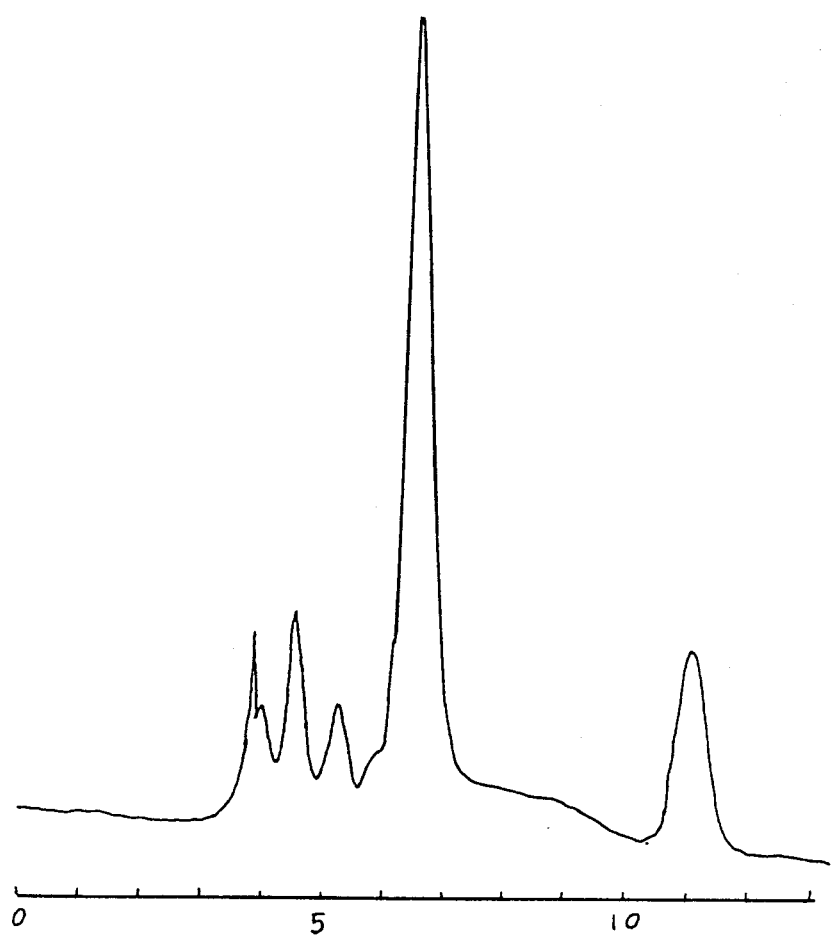

Similar procedures to those described in Example 1 were repeated by using respectively KBr and KI instead of KCl. On each occasion, the reaction solution was filtered and the filtrate was chromatographed by HPLC the charts shown in FIG. 6 or 7. The second peak from the right-hand side in FIG. 6 and the maxium peak in FIG. 7 shows respectively Pt(II)Br(D-gluc)(trans-l-dach) having the following elemental analysis: Calculated: H 3.95%, C 24.74% and N 4.81% Found: H 3.90%, C 25.02% and N 4.67% and Pt(II)I(D-gluc)(trans-l-dach) having the following elemental analysis: Calculated: H 4.10%, C 21.66% and N 4.21% Found: H 3.90%, C 21.67% and N 4.12%.

What is claimed is:

1. A platinum complex represented by the general formula (I):

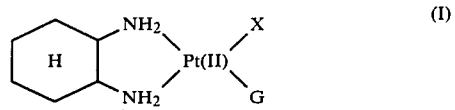

wherein X is a halogen atom and G is a glucuronic acid residue of the formula:

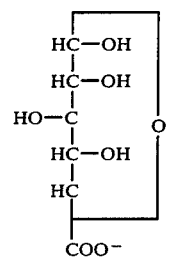

the configuration of diaminocyclohexane being selected from cis-, trans-l- and trans-d-forms.

2. The platinum complex of claim 1 wherein X is Cl.
3. The platinum complex of claim 1 wherein X is br.
4. The platinum complex of claim 1 wherein X is I.
5. The platinum complex of claim 1 wherein X is Cl and the diaminocyclohexane moiety is of the trans-l-configuration.

* * * * *